(12) United States Patent
Oliver

(10) Patent No.: US 6,679,124 B2
(45) Date of Patent: Jan. 20, 2004

(54) STATISTICALLY RIGID AND DYNAMICALLY COMPLIANT MATERIAL TESTING SYSTEM

(75) Inventor: Warren C. Oliver, Knoxville, TN (US)

(73) Assignee: MTS Systems Corporation, Eden Prairie, MN (US)

( * ) Notice: Subject to any disclaimer, the term of this patent is extended or adjusted under 35 U.S.C. 154(b) by 0 days.

(21) Appl. No.: 09/875,280

(22) Filed: Jun. 6, 2001

(65) Prior Publication Data

US 2002/0017146 A1 Feb. 14, 2002

Related U.S. Application Data

(60) Provisional application No. 60/209,553, filed on Jun. 6, 2000.

(51) Int. Cl.$^7$ ................................................. G01N 3/00
(52) U.S. Cl. ....................................................... 73/796
(58) Field of Search ........................ 73/760, 763, 774, 73/781, 788, 789, 790, 796

(56) References Cited

U.S. PATENT DOCUMENTS

| | | | | |
|---|---|---|---|---|
| 3,854,328 A | * | 12/1974 | Schmidt ........................ 73/813 |
| 3,927,558 A | * | 12/1975 | Philippe et al. ................ 73/816 |
| 4,084,322 A | * | 4/1978 | Albertazzi ...................... 33/517 |
| 4,297,884 A | | 11/1981 | Leveque et al. ............... 73/579 |
| 4,475,403 A | * | 10/1984 | Lentz ............................ 73/798 |
| 4,478,086 A | * | 10/1984 | Gram ............................ 73/781 |
| 4,848,141 A | | 7/1989 | Oliver ............................. 73/81 |
| 4,877,957 A | * | 10/1989 | Okada et al. ................. 250/306 |
| 5,195,378 A | * | 3/1993 | Ferguson ....................... 73/790 |
| 5,224,386 A | * | 7/1993 | Curtis ............................ 73/833 |
| 5,361,640 A | | 11/1994 | Carroll et al. ................. 73/831 |
| 5,693,890 A | | 12/1997 | Holmes ......................... 73/856 |
| 5,719,339 A | * | 2/1998 | Hartman et al. ............... 73/811 |

OTHER PUBLICATIONS

Meyers, Marc A., "Introduction to Mechanical Testing" in Metals Handbook®:American Society for Metals, edited by Boyer and Gall, 34.1–34.4, Metals Park, OH: American Society for Metals, 1985.
Pethica, J.B. and W.C. Oliver, "Mechanical Properties of Nanometre Volumes of Material: Use of the Elastic Reponse of Small Area Indentations" Materials Research Society Symposium Proceedings 130, 13–23, 1989.
Oliver, W.C. amd G.M. Pharr, "An improved technique for determining hardness and elastic modulus using load and displacement sensing indentation experiments" Journal of Materials Research, vol. 7, No. 6, 1564–1583, 1992.
Report prepared by D. Read, "Piezo–Actuated Microtensile Test Apparatus" Materials Reliability Division of the National Institute of Standards and Technology, Boulder, CO, pp. 255–259, circa 1996.
Lucas, B.N., W.C. Oliver and J.E. Swindeman, "The Dynamics of Frequency–Specific, Depth–Sensing Indentation Testing" Reprinted from Materials Research Society, Symposium Proceedings: Fundamentals of Nanoindentation and Nanotribology, vol. 522, Eds. Baker, S.P., N.A. Burnham, W.W. Gerberich and N.R. Moody).

* cited by examiner

Primary Examiner—Max Noori
(74) Attorney, Agent, or Firm—Westman, Champlin & Kelly, P.A.

(57) ABSTRACT

A material testing system includes a base and first and second specimen holders. A first displacement sensor measures displacement of the first specimen holder relative to the base. In addition, a second displacement sensor measures displacement of the second specimen holder relative to the base.

22 Claims, 2 Drawing Sheets

STATISTICALLY RIGID AND DYNAMICALLY COMPLIANT MATERIAL TESTING SYSTEM

The present application is based on and claims the benefit of U.S. provisional patent application Serial No. 60/209,553, filed Jun. 6, 2000, the content of which is hereby incorporated by reference in its entirety.

BACKGROUND OF THE INVENTION

The present invention relates to a dynamic testing system that applies force loads to a test specimen. More particularly, the present invention relates to a tensile testing system that applies tensile loads to a test specimen for the measurement of mechanical properties thereof.

Material testing systems that apply force loads to test specimens are known. Generally, such a system includes opposed holders that grip a specimen therebetween. An upper holder is joined to a crossbeam that moves relative to a lower holder. A load cell joined to the upper holder provides a signal indicative of tension or compression forces applied to the test specimen.

These material testing systems typically use a screw drive or hydraulic extension mechanism. The load cell for determining force used in these systems is chosen either for high sensitivity or for high load. Load cells with high rigidity however result in a lower sensitivity to displacement. Conversely, sensitive load cells can apply a lower maximum force to the test specimen.

Traditional testing machines however can not accommodate some test specimens of which mechanical properties are desired. In particular, the unique geometry of the test specimens and the dynamic mechanical properties desired makes the use of traditional material testing systems difficult, if not impossible. For example, determining mechanical properties of fibers with diameters of 1 to 60 microns is difficult with traditional testing systems. In addition, advances in polymer technology present the need for evaluation of tensile loaded materials beyond traditional yield, modulus and failure properties.

Accordingly, there is a need for a test system that can be used for small diameter test specimens. Results obtained therefrom can then be used to measure dynamic properties of these unique test specimens.

SUMMARY OF THE INVENTION

The present invention provides a material testing system having a base and first and second test specimen holders. A first displacement sensor measures displacement of the first specimen holder relative to the base. A second displacement sensor measures displacement of the second specimen holder relative to the base.

Another aspect of the present invention includes a material testing system having first and second specimen holders. A first actuator is coupled to the first specimen holder and a second actuator is coupled to the second specimen holder. A controller is coupled to the first and second actuators. The controller operates the first actuator to cause displacement of the first specimen holder and further operates the second actuator to dispose the second specimen holder in a known position.

In addition, a method is provided for determining elastic and plastic properties of materials. The method includes attaching a specimen to a first holder and a second holder and displacing the first holder away from the second holder. The method further includes applying a force to the second holder in a direction opposite displacement of the first holder and simultaneously measuring extension of the specimen with a first sensor and measuring force on the specimen with a second sensor.

DETAILED DESCRIPTION OF THE ILLUSTRATIVE EMBODIMENT

Figure 1:
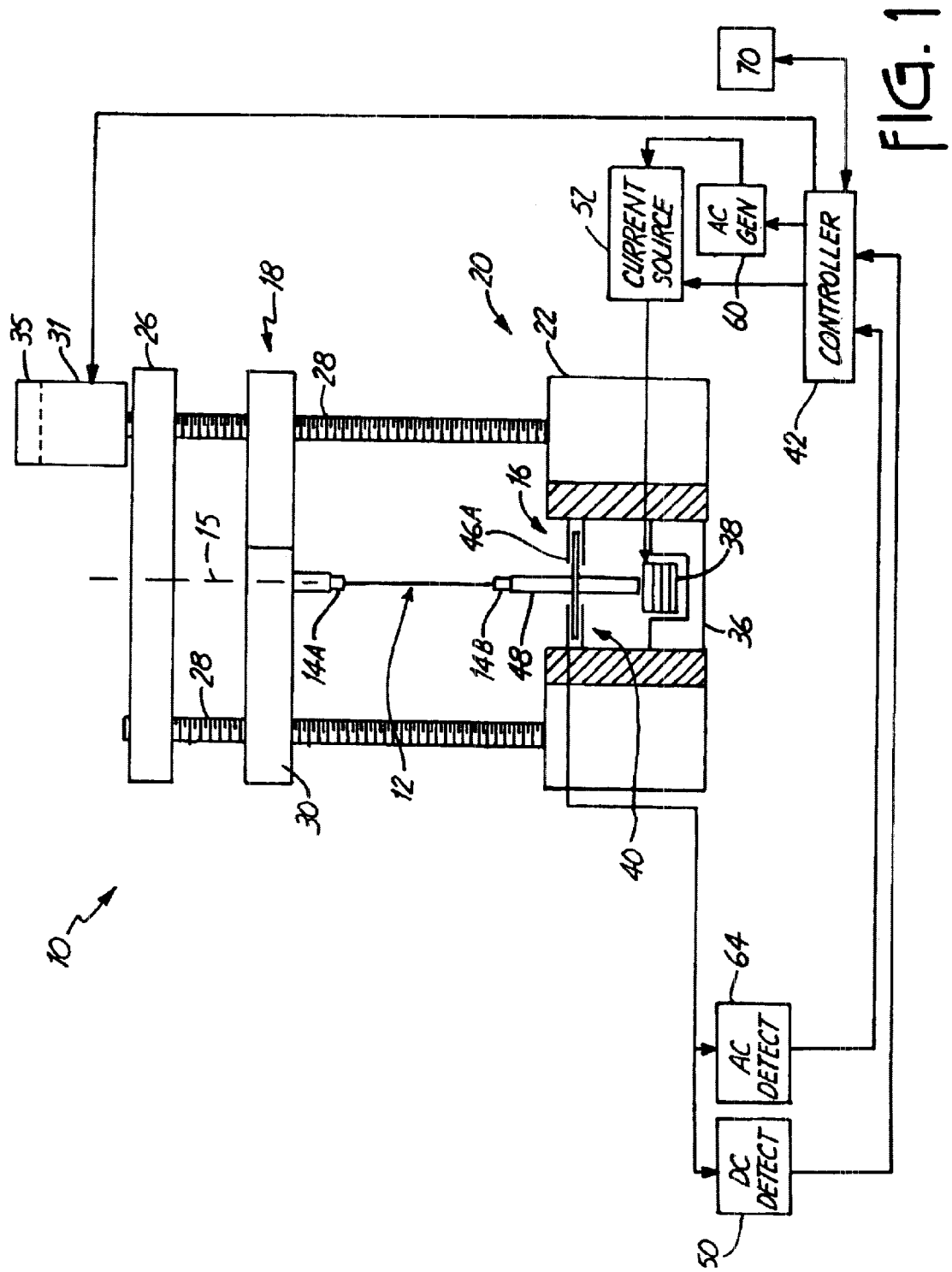
FIG. 1 illustrates a schematic view of a first exemplary embodiment of a material testing system according the present invention.

A material testing system 10 for applying loads to a test specimen 12 is illustrated in FIG. 1. The system 10 includes an upper specimen holder 14A and a lower specimen holder 14B that hold the test specimen 12 along a longitudinal axis 15. The lower specimen holder 14B is connected to a load-controlled, displacement sensing (LCDS) assembly 16 through which loads are provided to the test specimen 12 and reacted against a reaction structure generally indicated at 18. Although illustrated as a vertical testing system, the system 10 may be oriented horizontally or at other angles convenient for the test specimen 12.

In the exemplary embodiment illustrated, the material test system 10 includes a frame 20 having a base 22. A pair of threaded rods 28 extend upward from the base 22 to a crossbeam 26. The crossbeam 26 is generally fixed relative to the base 22. The reaction structure 18 can comprise a crosshead 30 that threadably mates with the threaded rods 28 and, therefore, is movable between the base 22 and the crossbeam 26. In the embodiment illustrated, a drive motor 31 rotates at least one of the threaded rods 28 in order to move the crosshead 30. A first displacement sensor 35 measures a position of the crosshead 30 relative to the frame 20.

The LCDS assembly 16 is used to measure loads applied to the test specimen 12 and/or provide a load and, in one embodiment, an oscillating load to the test specimen 12. As such, the load assembly 16 is coupled to the second specimen holder 14B and configured to control the second specimen holder 14B to be statically rigid and dynamically compliant. The LCDS assembly 16 includes a permanent magnet 36 mounted in the base 22, a coil 38 and a second displacement sensor 40. A controller 42 controls operation of the motor 31 and current to the coil 38. The controller 42 receives feedback signals from the first displacement sensor 35 and the second displacement sensor 40. The LCDS assembly 16 can also take other forms such as a pneumatic assembly, rather than the electromagnetic assembly herein illustrated.

As stated above, the first displacement sensor 35 measures displacement of the crosshead 30 relative to the frame 20 (i.e., the base 22 or the crossbeam 26). The first displacement sensor 35 generally measures elongation of the test specimen 12, which can be referenced to displacement of the crosshead 30 or the specimen holder 14A, whereas the specimen holder 14B is generally maintained in a fixed position. The first displacement sensor 35 can take many forms known in the art. For instance, the first displacement sensor 35 can include portions coupled to the frame 22 and the crosshead 30. Likewise, the first displacement sensor 35 can measure the distance between the crosshead 30 and the crossbeam 26. The first displacement sensor 35 can be an LVDT device, capacitive device, resistive device, optical device, etc., as are well known in the art. The first displacement device 35 can also be an encoder or other device (as illustrated) that senses rotation of the threaded rods 28 or the drive motor 31, wherein rotation is proportional to movement of the crosshead 30.

The second displacement sensor 40 is provided in order to control current provided to the coil 38. As discussed above, the specimen holder 14B is maintained in a fixed position. The second displacement sensor 40 senses the position of the specimen holder 14B. In the embodiment illustrated, the second displacement sensor 40 comprises a capacitive sensor generally known in the art, having a pair of fixed, stationary plates 46A with a movable plate 46B located therebetween. The movable plate 46B is coupled to a support shaft 48 which, in turn, is joined to the lower specimen holder 14B. Displacement of the support shaft 48 or specimen holder 14A is measured by the second displacement sensor 40, the output of which is connected to a DC displacement detector 50. The detector 50 digitizes the DC displacement signal, which is provided to the controller 42.

The system 10 is statically rigid and dynamically compliant thereby allowing high forces to be applied to the test specimen 12 and/or large extensions thereof, yet retaining high sensitivity. When a test is performed, the controller 42 provides a command signal to the drive motor 31 in order to move the crosshead 30 at a predetermined rate, thereby applying a load, in many cases to extend the test specimen 12. The controller 42 also controls a current source 52 that provides current to the coil 38. Current is provided to the coil 38 in order that the second displacement sensor 40 is maintained substantially in a fixed position. Thus, in one mode of operation, extension is measured via the first displacement sensor 35, discussed above, while load is measured from current provided to the coil 38. Use of the load and extension data allows the determination of stress, strain, yield, strength, ultimate tensile strength, and elastic modulus of the test specimen 12.

In addition, or alternatively, to a substantially static load provided by the drive motor 31 and/or the current source 52 for the coil 38, an oscillating load can also be provided. The oscillating load can be provided by superimposing an alternating current (AC) onto the drive current applied to the coil 38. The frequency of the oscillating force applied is typically in the range of from 0.5 to 200 Hz; however, depending on the design of the LCDS assembly 16, the concept can work from about 0.5 Hz to 1 MHz. The amplitude of the oscillating force may be in the range of from about $10^{-10}$ to 1 Newton, although forces less than or greater than this range can also be provided.

In FIG. 1, an AC signal generator 60 under control of the controller 42 injects or superimposes an AC signal into the output current signal of the current source 52. An AC displacement detector 64 detects the resulting AC displacement. The detector 64 may be a lock-in amplifier, which is tuned to measure the amplitude of the AC displacement at the applied frequency together with the phase of the displacement signal relative to the applied signal. The amplitude and phase signals are digitized by the detector 64 and provided to separate inputs of the controller 42 for analysis or storage in a mass storage device 70, along with the DC force and displacement, discussed above. Measurement of the resultant displacement oscillation and/or load, allows for continuous determination of the specimen damping and specimen stiffness, which provides a determination of the dynamic or viscoelastic properties of the specimen 12 as a function of extension, load, and frequency of applied oscillation.

The material testing system 10 decouples the load sensitivity from the load capacity by using the LCDS assembly 16. A suitable LCDS assembly 16 and capacitive displacement sensor 40 are available from the Nano Instruments Division of MTS Systems Corporation of Eden Prairie, Minn. Control of the load coil 38 and feedback from sensor 40 can be similar to that described in U.S. Pat. No. 4,848,141, which is hereby incorporated by reference.

In an embodiment illustrated, the second displacement sensor 40 is a capacitive displacement sensor, as described above, wherein the support shaft 48 is supported by very flexible leaf springs. Rather than depending on the deflection of a spring element in a conventional load cell in order to determine force, the system 10 is operated by using a feedback loop to maintain a known position of the support shaft 48, and thus the specimen holder 14B, by changing the current in the coil 38. This results in static rigidity (i.e., there is little or no deflection of the load mechanism associated with large deflections of the test specimen 12). In other words, this technique allows large forces and displacements (elongation) of the test specimen 12, while maintaining high sensitivity through measurement of current to the load coil 38. As discussed above, the known position of the specimen holder 14B can correspond to substantially zero displacement when only static loading is applied, alternatively, the known position can vary in time when an oscillatory force is applied.

An additional advantage to the system 10 is in the dynamic response. The dynamic response of the system 10 must be well known in order to extract the dynamic properties of the test specimen 12 from the data. In addition, the critical system dynamic properties must be of proper magnitude with relation to the desired test specimen response to ensure that the test specimen properties can be extracted. The transfer function that describes the response of the LCDS assembly 16 to an applied excitation is determined as a function of the support spring (capacitive displacement sensor 40) stiffness, the system damping, and the moving mass (e.g. support shaft 48, specimen holder 14B, load coil 38, etc.). These characteristics of the system must be well defined in order to solve for the specimen 12 stiffness and damping. If the system characteristics approach the magnitudes of those of the test specimen 12, errors in the determination of the system characteristics reduce the accuracy of the specimen data. Thus, for measurement of dynamic properties of the test specimen 12, the dynamic stiffness of the system must be very small when compared to the stiffness of the test specimen 12, which is provided in the system 10 of the present invention.

As appreciated by those skilled in the art, modifications of the system 10 can be made without significantly affecting system performance. For instance, instead of the threaded rods 28 and the drive motor 31, this actuator assembly can be of another mechanical form, such as a rack and pinion drive. In addition, a hydraulic or pneumatic actuator can be used to displace the crosshead 30 traveling on a suitable guideway. Likewise, a linear electric motor can also be used. In yet another embodiment, the LCDS assembly 16 and/or the displacement sensor 40 can be incorporated into the crosshead 30 to move therewith, wherein the lower specimen holder 14B is attached to the frame 20.

Figure 2:
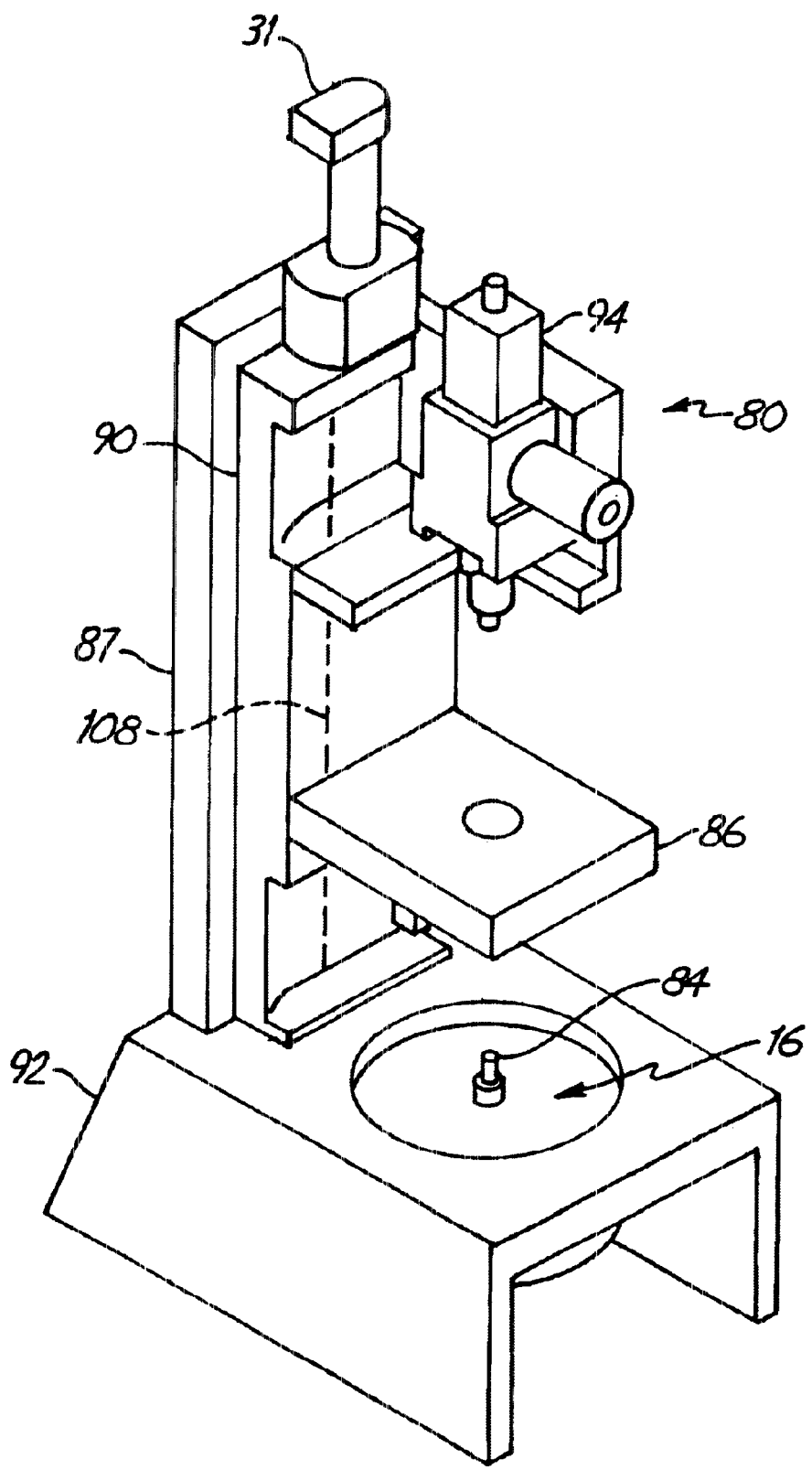
FIG. 2 illustrates a perspective view of an alternative embodiment of a material testing system according to the present invention.

As an example, FIG. 2 illustrates an alternative system 80 of the present invention. System 80 includes a first specimen holder (not shown, but mounted to a lower surface of a crosshead 86) and second specimen holder 84 that hold specimen 12 along an axis. The crosshead 86 is coupled to a support frame 87 through a suitable guide mechanism such as a linear bearing 108 (schematically illustrated). A drive motor 31 displaces the upper specimen holder relative to base 92 along support frame 87.

Lower specimen holder 84 is connected to the LCDS assembly 16 as previously described with reference FIG. 1. The upper specimen holder is coupled to crosshead 86. Drive motor 31 displaces upper specimen holder 82 relative to base 92. A displacement sensor within LCDS assembly 16 measures displacement of crosshead 86 along plate 90. An alignment microscope 94 can be provided in order to align the specimen holders 82 and 84 for the test specimen 12. Operation of system 80 is identical to system 10 described above.

Although the present invention has been described with reference to preferred embodiments, workers skilled in the art will recognize that changes may be made in form and detail without departing from the spirit and scope of the invention.

What is claimed is:

1. A material testing system comprising:
   a base;
   a first specimen holder;
   a second specimen holder, the first specimen holder and the second specimen holder being adapted to hold a specimen in tension;
   a first displacement sensor measuring displacement of the first specimen holder relative to the base along a common axis between the first and second specimen holders; and
   a second displacement sensor measuring displacement of the second specimen holder relative to the base along the common axis.

2. A material testing system comprising:
   a base;
   a first specimen holder;
   a second specimen holder, the first specimen holder and the second specimen holder being adapted to hold a specimen in tension;
   a first displacement sensor measuring displacement of the first specimen holder relative to the base along a common axis between the first and second specimen holders;
   a second displacement sensor measuring displacement of the second specimen holder relative to the base along the common axis; and
   an actuator assembly fixedly coupled to the second specimen holder and operated as a function of the second displacement sensor to dispose the second specimen holder in a known position.

3. The material testing system of claim 2 wherein the actuator assembly comprises an electromagnetic coil coupled to a current source.

4. The material testing system of claim 3 and further comprising a controller receiving a signal from the second displacement sensor and adjusting the current applied to the coil to maintain the second specimen holder in a stationary, known position.

5. The material testing system of claim 3 and further comprising a controller to vary the current applied to the coil to displace the second specimen holder in an oscillating manner.

6. A material testing system comprising:
   a base;
   a first specimen holder;
   a second specimen holder;
   a first displacement sensor measuring displacement of the first specimen holder relative to the base along a common axis between the first and second specimen holders; and
   a second displacement sensor measuring displacement of the second specimen holder relative to the base along the common axis, wherein the second displacement sensor is a capacitive sensor.

7. A material testing system comprising:
   a first specimen holder;
   a second specimen holder aligned with the first specimen holder along a common axis;
   a first actuator coupled to the first specimen holder;
   a second actuator coupled to the second specimen holder; and
   a controller coupled to the first actuator and the second actuator, the controller operating the first actuator to cause displacement of the first specimen holder away from the second specimen holder along the common axis, the controller further operating the second actuator to dispose the second specimen holder in a known position.

8. The material testing system of claim 7 wherein the second actuator includes a displacement sensor having a pair of fixed plates and a movable plate coupled to the second specimen holder.

9. The material testing system of claim 8 wherein the second actuator comprises an electromagnetic coil.

10. The material testing system of claim 9 wherein the second specimen holder is maintained in a fixed, known position.

11. The material testing system of claim 9 wherein an oscillatory force is applied to the second specimen holder.

12. The material testing system of claim 7 and further comprising a crosshead coupled to the first specimen holder, the crosshead further coupled to the first actuator.

13. The material testing system of claim 12 wherein the crosshead is coupled to a support frame with a guide mechanism to provide a predetermined path of displacement of the crosshead.

14. The material testing system of claim 13 wherein the guide mechanism comprises a linear bearing.

15. A method for determining elastic and plastic properties of materials, comprising:
   attaching a specimen to a first holder and a second holder, the first and second holders defining a common axis;
   displacing the first holder away from the second holder along the common axis;
   applying a force to the second holder in a direction opposite displacement of the first holder; and
   simultaneously measuring extension of the specimen with a first sensor measuring displacement of the first holder and measuring force on the specimen with a second sensor.

16. The method of claim 15 wherein the step of applying comprises maintaining the second holder in a first, fixed position.

17. The method of claim 15 wherein the step of applying comprises applying an oscillatory force to the second holder.

18. The method of claim 15 wherein an electromagnetic actuator is coupled to the second holder and the step of applying comprises applying a current to the electromagnetic actuator.

19. The method of claim 18 wherein measuring force on the specimen comprises measuring the current applied during the step of applying.

20. A material testing system comprising:

a first specimen holder;

a second specimen holder aligned with the first specimen holder along a common axis;

a first actuator coupled to the first specimen holder; a load assembly coupled to the second specimen holder and configured to control the second specimen holder to be statically rigid and dynamically compliant.

21. The material testing system of claim 20 wherein the load assembly comprises an electromagnetic coil coupled to a current source.

22. The material testing system of claim 20 wherein the load assembly includes a displacement sensor having a pair of fixed plates and a movable plate coupled to the second specimen holder.

* * * * *